United States Patent [19]

Hertzenberg

[11] Patent Number: 4,626,550

[45] Date of Patent: Dec. 2, 1986

[54] ZEOLITE FOR PERSONAL CARE PRODUCTS

[75] Inventor: Elliot P. Hertzenberg, Wilmington, Del.

[73] Assignee: PQ Corporation, Valley Forge, Pa.

[21] Appl. No.: 785,373

[22] Filed: Oct. 7, 1985

Related U.S. Application Data

[63] Continuation-in-part of Ser. No. 691,093, Jan. 14, 1985, abandoned.

[51] Int. Cl.$^4$ .............................................. A61K 7/16
[52] U.S. Cl. ...................................... 514/770; 424/49; 424/52; 424/57; 424/78; 514/949
[58] Field of Search .................. 424/52, 57, 49, 78; 514/949, 770

[56] References Cited

U.S. PATENT DOCUMENTS

| | | |
|---|---|---|
| 2,882,243 | 4/1959 | Milton .............................. 260/448 C |
| 3,250,680 | 5/1966 | Menkart et al. ....................... 424/49 |
| 4,141,186 | 2/1979 | Schoofs .................................. 52/172 |
| 4,151,690 | 5/1979 | Schoofs .................................. 52/172 |
| 4,159,316 | 6/1979 | Januszewski et al. ................. 424/49 |
| 4,187,287 | 2/1980 | Schreiber et al. ..................... 424/49 |
| 4,193,987 | 3/1980 | Harth et al. ............................ 424/49 |
| 4,209,504 | 6/1980 | Harth et al. ............................ 424/49 |
| 4,349,533 | 9/1982 | Dent et al. ............................. 424/49 |
| 4,362,715 | 12/1982 | Strianse et al. ....................... 424/63 |
| 4,379,143 | 4/1983 | Sherry et al. ........................ 424/154 |
| 4,537,771 | 8/1985 | Greb et al. .......................... 424/154 |

FOREIGN PATENT DOCUMENTS 57-158286  9/1982  Japan ..................................... 71/903

*Primary Examiner*—Ronald W. Griffin
*Attorney, Agent, or Firm*—Ernest G. Posner; J. S. Stephen Bobb; Fred C. Philpitt

[57] ABSTRACT

Self-warming personal care products such as lotions, creams and pastes can be prepared using Zeolite A that contains both sodium and potassium.

6 Claims, No Drawings

ZEOLITE FOR PERSONAL CARE PRODUCTS

This application is a continuation in part of my U.S. patent application Ser. No. 691,093, filed Jan. 14, 1985, now abandoned.

BACKGROUND OF THE INVENTION

This invention relates to zeolites as ingredients to provide warming in personal care products in the form of lotions, ointments, creams and the like. More particularly, this invention involves Zeolite A that has been treated to substantially reduce adsorption of gases.

Personal care products are often solutions, suspensions or emulsions of various ingredients in appropriate vehicles to provide lotions, ointments and creams of the proper rheology to be applied. These products include toothpastes, facial creams, medicated creams, cleansing creams, analgesic balms, cosmetic lotions and the like. Zeolites have been included as ingredients in personal care products such as toothpastes (U.S. Pat. Nos. 4,349,533; 4,159,316; 4,187,287 and 3,250,680), cleansing and medicated creams (U.S. Pat. Nos. 4,362,715 and 3,250,680), analgesic balms (U.S. Pat. No. 4,379,143) and others. In these products the zeolites function as abrasives, astringents, carriers, deodorants and as sources of heat for self-warming products.

The self-warming products require that the zeolite be activated so that it releases heat upon adsorbing water when applied. A problem that has been found when activated zeolites have been tried in such formulations is swelling upon aging or other environmental factors. This swelling, which can bulge and burst the container as well as changing the texture of the product, is caused by degassing of the zeolite (see U.S. Pat. No. 4,159,316). Activated zeolites readily adsorb non-polar gases, particularly nitrogen. When the gases are replaced in the zeolite by some other constituent, or by a change in temperature, swelling results. Some products can be formulated so that none of the ingredients will replace the gas. This expedient does not prevent degassing because of environmental factors, and severely limits the materials available in formulating the desired product. Heating the partial or completed composition can remove the gas, but there is a risk in changing the ingredients. A better solution would be to provide a zeolite that does not adsorb nitrogen.

Several investigators have found that Zeolite A in the potassium form does not adsorb nitrogen or oxygen (see page 113 of Peterson's "Influence of Presorbed Water on the Sorption of Nitrogen at Ambient Temperatures," ACS Symposium Series 135, American Chemical Society, Washington, DC, 1980). Such potassium form zeolites have been used in adsorbent combinations for sealed thermal windows (see U.S. Pat. Nos. 4,151,690 and 4,141,186).

It is an object of this invention to provide a form of Zeolite A that contains both sodium and potassium, in such a manner that the zeolite does not adsorb gases and has a high heat release on hydration and is suitable for personal care products. It is a further object of this invention to provide a Zeolite A that contains sodium and potassium in such a manner that the zeolite can be pH-adjusted while maintaining a high heat release upon hydration. Such pH-adjusted materials are often required for personal care products.

The prior art patents usually indicate the sodium form of Zeolite A as useful in these warming compositions. It is well recognized that Zeolite A can be treated so that it contains various metals such as calcium and the like. Such materials also sorb and desorb gases in an undesirable manner. It is a further object of this invention to provide a Zeolite A that may contain sodium and other metals with potassium so that the zeolite does not sorb gases and has a high heat release when moistened.

SUMMARY OF THE INVENTION

I have found that personal care products such as lotions and creams that are prepared using Zeolite A that contains sodium and potassium, or sodium, other metals and potassium, of certain levels do not swell upon aging or on temperature changes. Further, such a zeolite releases sufficient heat upon hydration to produce the desired warming effect. I have also found that Zeolite A with certain ratios of sodium to potassium content can be pH-adjusted to provide a less basic material for these personal care products. After the Zeolite A has had its sodium-potassium ratio adjusted and, if desired, pH-adjusted, it is activated by heating to a level that removes the volatile materials (usually water) but does not decompose the zeolite. These zeolites can be combined with materials usually found in personal care products as long as they are essentially anhydrous and do not cause a heat release when mixed with the zeolite.

The generation and maintenance of the heat of hydration of the zeolite in a personal care product can be controlled by varying the character of the largest component of the product—the vehicle in which the functional ingredients are dispersed. If a quick, strong release of heat is required, a hydrophilic vehicle of low viscosity is used. A slower, more sustained heat release may be realized by using a vehicle with increased hydrophobic character and a higher viscosity.

THE INVENTION

The zeolites required for compositions of my invention are crystalline aluminosilicates of the structure referred to as Zeolite A. The preparation and properties of these zeolites are described in detail in U.S. Pat. No. 2,882,243, among other sources. This patent is incorporated herein by reference. Generally, the preparation involves combining aqueous solutions that are sources of silica, alumina and sodium to produce a gel which crystallizes upon hydrothermal treatment. Conventional washing and drying steps provide hydrated Zeolite NaA. Heating this product to a temperature above about 300° C. provides a zeolite that has a strong heat of hydration but also adsorbs gases, in particular nitrogen from air. The hydrated Zeolite NaA can be treated to incorporate other metal ions such as Ca and Mg into its structure. Such Zeolites wherein part of the sodium is replaced with a metal ion other than potassium, and said zeolite still sorbs and desorbs gases, are useful starting materials for preparing the composition of my invention.

The hydrated Zeolite NaA must be modified with the substitution of potassium for part of the sodium prior to activation. The potassium modification is carried out by ion exchange in aqueous solution using nearly any appropriate potassium salt such as $KCl$, $KNO_3$ $K_2SO_4$ and the like. The exchange can be carried out in any convenient manner that allows control of the amount of potassium exchanged for sodium, or for sodium with other metals.

The zeolite required for my invention must have sufficient potassium exchanged for sodium to prevent adsorption of nitrogen from the air. The exchange can be carried to any higher level desired. Up to 80% exchange can be effective; I prefer the zeolite to have about 25 to 60% of the sodium replaced with potassium. I most prefer that about 30 to 50% by potassium. Washing, filtering and calcining (about 300° to 600° C. for a sufficient time to remove all water) completes the preparation of these so-called activated materials. The zeolites resulting from this process can be conveniently represented by the following notation:

$$\text{Zeolite}(K_xNa_{12-x})A$$

wherein x can be about 3 to 9.6, with about 3.0 to 7.2 or about 3.6 to 6.0 corresponding to the preferred and most preferred levels of exchange, respectively. Another form of notation for such exchanged products is sometimes employed. It is:

$$\text{Zeolite KNaA—nn}$$

wherein nn represents the degree in percent of exchange of potassium for sodium. For the preferred range of exchange nn is 25 to 60, while for the most preferred range nn is 30 to 50. The second notation is used in my examples.

Zeolites are alkaline materials, and in some personal care products such strong alkalinity is a disadvantage. In these products pH-adjusted zeolites with the proper potassium/sodium balance are useful. The pH adjustment is carried out after the potassium exchange. The potassium content for these materials prior to the pH treatment can be somewhat less than that of the previous materials described. Such zeolites can be represented by the notation: $\text{Zeolite}(K_xNa_{12-x})A$, wherein x can be 1.8 to 9.6. In the second notation system this range would be Zeolite KNaA-15 to Zeolite KNaA-80. The exchanged zeolites are pH-adjusted by slurrying in water and adding acid slowly until the pH is between about 5.0 and 9.5. Mineral acids such as $H_2SO_4$ and HCl are usually used for this technique. The acidified slurry is aged for 30 to 90 minutes. Washing, filtering, drying and calcining complete the preparation. The composition of zeolites treated in this manner can be represented as:

$$\text{Zeolite}[K_xNa_{12-(x+y)}H_y]A$$

wherein x is about 1.8 to 9.6 and y is about 0.6 to 2.2, and preferably x can be 1.8 to 3.8 with y being 0.6 to 2.2.

Other conventional ingredients of personal care products can be employed for their usual function. Such ingredients can include dyes, perfumes, surface active agents, fillers, abrasives, polishing agents, thickeners, flavorings, sweeteners, bodying agents, topical pain relievers, antiperspirants and others. These materials must be largely anhydrous and should not enter the structures of the zeolite to release heat.

The zeolite(s) and other functional ingredients are compounded with or suspended in various carriers or vehicles which constitute a large proportion of the composition. Depending upon the interaction with the functional ingredients, including zeolite, it is usually the vehicle that determines the form of the product—liquid, cream or paste. These materials must be largely anhydrous, and they should not enter the cages of the zeolite to release heat. Interaction between the zeolite and the vehicle should not be exceptionally strong. For instance, if a vehicle and a zeolite interact to provide a very high viscosity, water would disperse very slowly in the material, and the heat release would not be realized as required. Useful vehicles include hydrocarbons, polyalkylene glycols such as triethylene glycol and tripropylene glycol, peanut oil, cetyl alcohol, stearyl alcohol, glyceryl monostearate, stearic acid, petrolatum, mineral oil, methyl paraben and the like. These materials should contain less than 3.0% water, and preferably less than 1.5%.

One of the most important aspects to be considered when selecting the liquid vehicle or carrier is the way in which the liquid interacts with water. If the liquid vehicle is hydrophilic, completely miscible with water, moisture becomes distributed throughout the liquid, and the zeolite becomes hydrated and releases its heat very rapidly. If the liquid vehicle is hydrophobic, immiscible with water, moisture diffuses into the liquid slowly, and the heat release is delayed, but may be sustained for a longer period of time. The heat released upon hydration of the zeolite can be controlled by changing the hydrophobic-hydrophilic nature of the liquid vehicle. For example, a hydrophobic vehicle could be modified by adding a surfactant to introduce more water compatibility. As the proportion of surfactant is increased, water diffuses faster in the liquid and the zeolite hydrates more quickly with a resultant faster release of heat.

The release of heat upon moisture addition to my composition can also be controlled by coating the zeolite with either a material that must be dissolved before water can enter the zeolite cage or a partially hydrophobic material that delays water intrusion into the cages.

The personal care products of my invention may contain a number of ingredients in addition to the zeolite and the vehicle. However, the zeolite and the anhydrous liquid vehicle constitute the largest proportion of the product, and it is important that they be in appropriate relationship so that the desired warming be realized. Suitable zeolite/vehicle combinations include 1 to 6 pbw of activated zeolite and 4 to 9 pbw of said vehicle. Other ingredients may be present in amounts up to 6 pbw.

As indicated previously, the potassium exchange is effective in reducing or eliminating the sorption of gases in type A zeolite that contain metals in addition to sodium. These metals can be any that do not interfere with the potassium exchange and do not significantly diminish the heat released when water contacts the activated zeolite. For example, a Zeolite A with a metal ion content of 48.5% Mg and 51.5% Na had a nitrogen desorption of 5.3 ml/g. After potassium exchange the metal content was 45.6% Mg, 16.6% Na and 37.8% K and the nitrogen desorption was 0.2 ml/g. Similarly, a zeolite with a metal content of 7.6% Ca, 37% Na and 55.4% K exhibited no desorption of Na. After activation both zeolites had heat releases upon water addition that were about the same as zeolites containing only sodium and potassium.

The products of my invention are stable creams, lotions and pastes which, when applied to the skin or other suitable tissues, become warm as moisture is drawn from the surroundings into the zeolite to release heat. Under dry conditions it may be necessary to wet the skin. The creams, lotions and pastes are stable. They do not swell or burst their containers upon aging, heating and/or cooling or other environmental conditions.

EXAMPLES

The following examples illustrate certain embodiments of my invention. These examples are not provided to establish the scope of the invention, which is described in the disclosure and recited in the claims. The proportions are in parts by weight (pbw) unless otherwise indicated.

EXAMPLE 1

Samples of potassium-containing Zeolite A, having varied levels of potassium exchange of the initially present sodium, were prepared by treatment of sodium Zeolite A (called NaA) with a potassium chloride solution. The potassium-exchanged products will be designated by the term KNaA-nn, where nn is the degree of potassium exchange; for example, 24% exchanged product will be described as KNaA-24.

The Zeolite NaA starting material for the potassium exchange is a highly crystalline fine powder having 4.3 micron mean particle size. To prepare the potassium-exchanged zeolites, 1 pbw NaA was slurried with varied quantities of an aqueous solution of KCl under agitation for 10 minutes, followed by filtration, washing with water, drying, and gentle milling so as to produce a finely dispersed powder. The quantity of KCl reacted and the resultant KNaA products are shown below.

TABLE 1

| Reactants (pbw KCl/1 pbw NaA) | Product |
|---|---|
| 0.051 | KNaA-11 |
| 0.081 | KNaA-18 |
| 0.134 | KNaA-24 |
| 0.191 | KNaA-29 |
| 0.273 | KNaA-36 |
| 0.497 | KNaA-45 |
| 1.629 | KNaA-74 |

The NaA starting material and the KNaA products were activated (dehydrated) at 475° C. overnight in air. The activated KNaA products all had an ignition loss of 1.5% or lower, while the activated NaA had a 1.7% ignition loss.

EXAMPLE 2

Portions of the KNaA products and NaA starting material from Example 1 were pH-adjusted by careful treatment with diluted sulfuric acid. A 10% slurry of zeolite in water was prepared, and while under vigorous agitation, was treated with 4N $H_2SO_4$ very slowly until pH 6.0 was reached. The addition of acid usually occurred over a 40–50 minute period. The zeolite product was then isolated from the slurry as described in Example 1. Chemical analysis results showed that the pH-adjustment step led to approximately 10–15% replacement by hydronium ion for the initially present sodium and potassium ion in the zeolite.

TABLE 2

| % K-Exchange in KNaA Starting Material | % K-Exchange in KHNaA (pH 6) Product |
|---|---|
| 11 | 11 |
| 18 | 15 |
| 24 | 22 |
| 29 | 29 |
| 36 | 32 |
| 45 | 37 |
| 74 | 64 |

The KNaA and KHNaA zeolites were slurried in water (1.3 pbw in 100 pbw water) and the pH was measured. Sodium bromide was then added to the slurry in a quantity appropriate to provide a 0.1N electrolyte concentration. The pH of the slurry was then remeasured.

TABLE 3

| | pH of Slurry | |
|---|---|---|
| Zeolite | No Electrolyte | 0.1 N Electrolyte |
| NaA | 10.9 | 10.7 |
| KNaA-11 | 10.9 | 10.6 |
| KNaA-18 | 10.6 | 10.5 |
| KNaA-24 | 10.6 | 10.5 |
| KNaA-29 | 10.7 | 10.5 |
| KNaA-36 | 10.8 | 10.5 |
| KNaA-45 | 10.8 | 10.4 |
| KNaA-74 | 10.7 | 10.4 |
| NaHA | 10.0 | 7.4 |
| KHNaA-11 | 10.0 | 7.4 |
| KHNaA-15 | 9.8 | 7.2 |
| KHNaA-22 | 9.5 | 7.2 |
| KHNaA-29 | 9.5 | 6.9 |
| KHNaA-32 | 9.2 | 6.8 |
| KHNaA-37 | 9.1 | 6.5 |
| KHNaA-64 | 9.1 | 6.3 |

The KNaA products are alkaline. The pH-adjusted zeolites are less alkaline in pure water, and in the presence of electrolyte the pH is lowered into the neutral range (due to ion exchange release of hydronium ion by the added sodium cation).

The KHNaA products were activated at 475° C. in air. The KNaHA products all had ignition loss of 1.0% or lower, whereas the NaHA product had a 1.4% ignition loss.

EXAMPLE 3

An anhydrous ointment base was prepared; 1 pbw activated zeolite was blended into 3 pbw mineral oil to produce a paste. A portion (40 g) of the paste was placed along with a magnetic stirrer into a flask, which was then connected to an apparatus that measures gas evolution via displacement of water inside an inverted graduated cylinder. The flask was then heated at 100° C. under agitation by the stirrer until evolution of nitrogen gas was completed. A similar measurement of gas evolution was done with 10 g zeolite powder (equivalent to the quantity of zeolite in the paste), except that use of the magnetic stirrer was not required.

TABLE 4

| | Volume Release of Gas (milliliters) | |
|---|---|---|
| Zeolite | From Powder | From Paste |
| NaA | 50 | 40 |
| KNaA-11 | 38 | 35 |
| KNaA-18 | 29 | 23 |
| KNaA-24 | 14 | 19 |
| KNaA-29 | 11 | 10 |
| KNaA-36 | 0 | 0 |
| KNaA-45 | 0 | 0 |
| KNaA-74 | 0 | 0 |
| NaHA | 45 | 34 |
| KHNaA-11 | 38 | 40 |
| KHNaA-15 | 16 | 18 |
| KHNaA-22 | 0 | 0 |
| KHNaA-29 | 0 | 0 |
| KHNaA-32 | 0 | 0 |
| KHNaA-37 | 0 | 0 |
| KHNaA-64 | 0 | 0 |

These results show that KNaA does not adsorb and subsequently desorb gas if the potassium exchange is above about 33%; at exchange levels below about 33%, the amount of desorbed gas decreases as the exchange is increased. The pH-adjusted zeolite, KHNaA (pH 6.0), no longer desorbs gas when the potassium-exchange level is above about 20%.

EXAMPLE 4

A simple test for the relative heat release of the KNaA and KHNaA powder was conducted as follows:
1. Weigh 60 g water into a 150 mL plastic beaker, and measure the temperature of the water.
2. Add 31.2 g zeolite rapidly to the water, using the thermometer to wet the zeolite as rapidly as possible.
3. Note the maximum temperature that is reached, and then calculate the temperature rise ($\Delta T$).

TABLE 5

| Zeolite | $\Delta T$ max |
|---|---|
| NaA | 38 |
| KNaA-11 | 33 |
| KNaA-18 | 33 |
| KNaA-24 | 32 |
| KNaA-29 | 31 |
| KNaA-36 | 32 |
| KNaA-45 | 32 |
| KNaA-74 | 33 |
| NaHA | 35 |
| KNaHA-11 | 34 |
| KNaHA-15 | 33 |
| KNaHA-22 | 30 |
| KNaHA-29 | 30 |
| KNaHA-32 | 26 |
| KNaHA-37 | 19 |
| KNaHA-64 | 2 |

These results show that the KNaA releases slightly less heat than NaA, but the heat release is not affected by the K-exchange level. The KHNaA (pH 6.0) shows good heat release up to about 30% K-exchange, but the heat release property decreases rapidly above that level due to increasing destruction of the zeolite crystal lattice during the activation step.

When the zeolite-mineral oil paste containing the zeolite with good heat release properties was rubbed onto the skin, a sustained release of heat was felt.

EXAMPLE 5

Portions of the unactivated KNaA products (from Example 1) were treated with diluted sulfuric acid, as in Example 2, except that addition of acid was stopped when pH 7.0 was reached. This pH-adjustment step led to approximately 8-10% replacement of sodium and potassium ion by hydronium ion.

The pH of the KHNaA zeolites was measured in water and 0.1N electrolyte, as described in Example 2. In pure water, the pH values were in the 9.8-10.1 range. In 0.1 NaBr electrolyte, the pH values were in the 7.2-7.7 range.

The KHNaA (pH 7.0) products were heated at 475° C. in air. The resultant activated products all had ignition loss of 1.5% or lower.

The KHNaA (pH 7.0) shows good heat release up to about 50% K-exchange, but the heat release property decreases rapidly above that level of exchange.

EXAMPLE 6

Portions of the unactivated KNaA products (from Example 1) were treated with diluted sulfuric acid, as in Example 2, except that addition of acid was stopped when pH 8.0 was reached. This pH-adjustment step led to approximately 5-7% exchange of hydronium ion for the sodium and potassium ions.

When slurried in water, the KHNaA zeolites gave pH values in the 10.1-10.3 range. In 0.1N NaBr electrolyte, the pH values were in the 8.2-8.6 range.

The KHNaA (pH 8.0) products were heated in air at 475° C. The resultant activated products all had ignition loss of 1.1% or lower.

The KHNaA (pH 8.0) shows good heat release up to about 70% K-exchange, but the heat release property decreases rapidly at higher levels of K-exchange.

EXAMPLE 7

A sample of KHNaA (pH 7.0) was prepared by treating a 10% aqueous slurry of NaA with an aqueous slurry of KCl, in the reactant ratio 0.273 pbw KCl/1 pbw NaA, followed immediately by pH-adjustment to pH 7.0 with diluted sulfuric acid. After 60 minutes of equilibration, the zeolite was filtered, washed with water, and dried. Chemical analysis showed that the product was 34% K-exchanged and 11% hydronium-exchanged. This product gave pH 10.3 when slurried in water, and pH 8.0 in 0.1N NaBr electrolyte solution.

Upon activation at 475° C., the KHNaA product had a 1.0% ignition loss and it did not desorb gas upon heating at 100° C. This product had good heat release, giving 30° C. $\Delta T$ max.

EXAMPLE 8

A sample of KHNaA (pH 8.0) was prepared by the method described in Example 7, except that the acid addition was ended when the pH dropped down to 8.0. Chemical analysis showed that the product was 35% K-exchanged and 5% hydronium-exchanged. This product gave pH 10.3 in pure water and pH 9.8 in 0.1N NaBr electrolyte.

Upon activation, the KHNaA product had 0.5% ignition loss and it did not desorb gas upon heating at 100° C. This product has good heat release, giving 30° C. $\Delta T$ max.

We claim:

1. A self-warming personal care product in the form of a lotion, ointment, paste or cream comprising 1 to 6 parts by weight (pbw) of activated Zeolite A and 4 to 9 pbw of an anhydrous liquid vehicle, said zeolite being defined by the notation:

$$\text{Zeolite}(K_x Na_{12-x})A$$

wherein x is about 3.0 to 7.2.

2. The personal care product of claim 1 containing Zeolite $(K_x Na_{12-x})A$ wherein x is about 3.6 to 6.0.

3. The personal care product of claim 2 wherein the zeolite has a portion of the sodium replaced by another metal that does not interfere with potassium ion exchange and does not diminish the heat released when water contacts the zeolite.

4. The personal care product of claim 1 wherein the zeolite has a portion of the sodium replaced by another metal that does not interfere with potassium ion exchange and does not diminish the heat released when water contacts the zeolite.

5. A self-warming personal care product in the form of a lotion, ointment, paste or cream comprising 1 to 6 parts by weight (pbw) of activated pH-adjusted, potassium exchanged Zeolite A and 4 to 9 pbw of an anhydrous liquid vehicle, said zeolite being defined by the notation:

Zeolite$[K_xNa_{12-(x+y)}H_y]A$ wherein x is about 1.8 to 3.8 and y is about 0.6 to 2.2.

6. The personal care product of claim 5 wherein the zeolite has a portion of the sodium replaced by another metal that does not interfere with potassium ion exchange and does not diminish the heat released when water contacts the zeolite.

* * * * *